United States Patent [19]
Lamatsch et al.

[11] Patent Number: 5,874,588
[45] Date of Patent: Feb. 23, 1999

[54] PROCESS FOR THE PREPARATION OF DIKETOPYRROLOPYRROLECARBOXYLIC ACIDS AND THEIR ESTERS AND AMIDES

[75] Inventors: Bernd Lamatsch; Olof Wallquist, both of Marly, Switzerland

[73] Assignee: Ciba Specialty Chemicals Corporation, Tarrytown, N.Y.

[21] Appl. No.: 933,591

[22] Filed: Sep. 19, 1997

[30]  Foreign Application Priority Data

Sep. 19, 1996 [CH] Switzerland ............... 2298/96

[51] Int. Cl.⁶ ............ C07D 487/02; C07D 209/02; C07D 233/60; C07D 233/58
[52] U.S. Cl. .......... 548/453; 548/453; 548/454; 548/455; 548/467; 548/341.5; 548/519; 548/400; 548/255; 548/335.5; 548/375.1; 548/440; 548/490; 548/363.1; 568/735; 546/184; 546/153; 544/358; 544/106; 544/59
[58] Field of Search ............... 548/453, 455, 548/456, 454, 467, 341.5

[56]  References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,791,204 | 12/1988 | Jost et al. | 548/101 |
| 5,476,886 | 12/1995 | Wallquist et al. | 524/92 |

*Primary Examiner*—Johann Richter
*Assistant Examiner*—Dominic Keating
*Attorney, Agent, or Firm*—Kevin T. Mansfield

[57] ABSTRACT

Diketopyrrolopyrroles of formula I

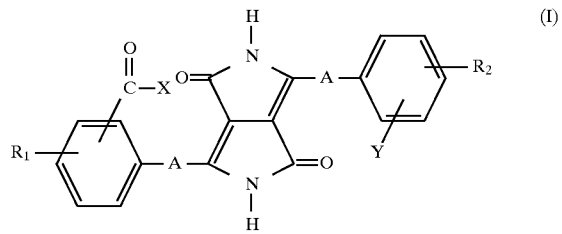

are prepared by reacting a diketopyrrolopyrrole of formula II

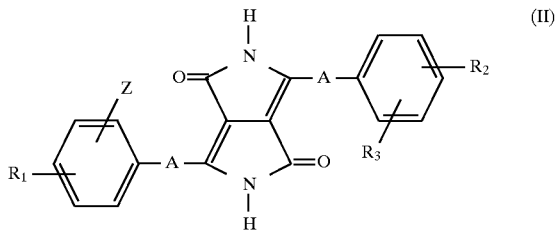

with a) formic acid or b) a compound of formula III $$X'-H \quad (III)$$

or with an alkali metal formate or alkaline earth metal formate together with carbon monoxide in the presence of a catalyst, wherein, in formulae I, II and III, A is a direct bond or a group

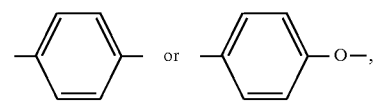

wherein phenylene is bound to the pyrrolopyrrole, $R_1$, $R_2$ and $R_3$ are each independently of one another hydrogen, halogen, $C_1$–$C_6$alkyl, $C_5$–$C_6$cycloalkyl, $C_1$–$C_6$alkoxy, $C_1$–$C_6$alkylamino, $C_1$–$C_6$alkylmercapto, —$CF_3$, —CN or —$NO_2$, X is X' or OH, X' is —$OR_4$ or —$N(R_5)(R_6)$, wherein $R_4$ is $C_1$–$C_{18}$alkyl, $C_5$–$C_6$cycloalkyl; phenyl or naphthyl which is unsubstituted or substituted by halogen, $C_1$–$C_6$alkyl, $C_1$–$C_6$alkoxy, $C_1$–$C_6$alkylamino, —CN or —$NO_2$, $R_5$ and $R_6$ are each independently of the other hydrogen, $C_1$–$C_{18}$alkyl, $C_5$–$C_6$cycloalkyl; phenyl or naphthyl which is unsubstituted or substituted by halogen, $C_1$–$C_6$alkyl, $C_1$–$C_6$-alkoxy, $C_4$–$C_6$alkylamino, —CN or —$NO_2$, or a group —$(CH_2)_n$—$SO_3R_7$, wherein $R_7$ is hydrogen, potassium or sodium, and n is an integer from 2 to 6, or $R_5$ and $R_6$, together with the linking nitrogen atom, are an unsubstituted or $C_1$–$C_6$alkyl- or phenyl-substituted 5- or 6-membered heterocyclic radical selected from the group consisting of pyrrolidinyl, piperidyl, pyrrolyl, triazolyl, imidazolyl, pyrazolyl, piperazinyl, morpholinyl, thiomorpholinyl, phthalimidyl, carbazolyl, indolyl, indazolyl, benzimidazolyl and tetrahydroquinolinyl, Y is $R_3$ or

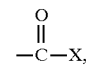

and Z is halogen.

13 Claims, No Drawings

PROCESS FOR THE PREPARATION OF DIKETOPYRROLOPYRROLECARBOXYLIC ACIDS AND THEIR ESTERS AND AMIDES

The present invention relates to the preparation of diketopyrrolopyrrolecarboxylic acids and their esters and amides, starting from diketopyrrolopyrrolehalogen compounds.

U.S. Pat. Nos. 4,415,685, 4,579,949 and 4,791,204 disclose diketopyrrolopyrrolecarboxylic acids and the esters and amides thereof which are prepared by reacting dialkyl succinates with benzonitriles substituted by a corresponding carboxylic acid group, carboxylate group or carboxamide group, which benzonitriles are usually difficult to access. Diketopyrrolopyrrolecarboxamides are also described in U.S. Pat. No. 5,476,886. They are obtained from corresponding diketopyrrolopyrrolecyano derivatives by addition of concentrated sulfuric acid.

It is therefore the object of this invention to provide an improved process for the preparation of diketopyrrolopyrrolecarboxylic acids and their esters and amides, starting from diketopyrrolopyrrolehalogen compounds. This process should, in particular, make it possible to obtain the compounds of this invention in higher yields and higher chemical purity and having excellent chroma.

Accordingly, an improved process has been found for the preparation of diketopyrrolopyrroles of formula I

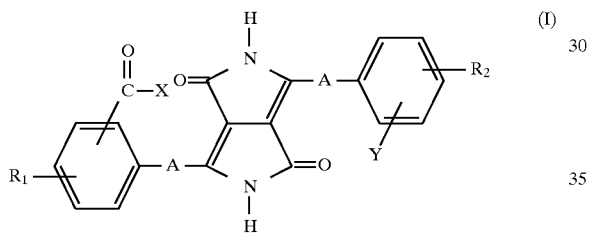

by reacting a diketopyrrolopyrrole of formula II

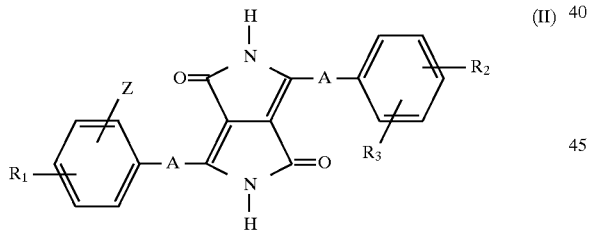

with
a) formic acid or
b) a compound of formula III

or with an alkali metal formate or alkaline earth metal formate together with carbon monoxide
in the presence of a catalyst,
wherein, in formulae I, II and III,
A is a direct bond or a group

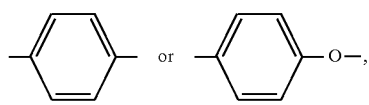

wherein phenylene is bound to the pyrrolopyrrole, $R_1$, $R_2$ and $R_3$ are each independently of one another hydrogen, halogen, $C_1$–$C_6$alkyl, $C_5$–$C_6$cycloalkyl, $C_1$–$C_6$alkoxy, $C_1$–$C_6$alkylamino, $C_1$–$C_6$alkylmercapto, —$CF_3$, —CN or —$NO_2$, X is X' or OH, X' is —$OR_4$ or —$N(R_5)(R_6)$, wherein $R_4$ is $C_1$–$C_{18}$alkyl, $C_5$–$C_6$cycloalkyl; phenyl or naphthyl which is unsubstituted or substituted by halogen, $C_1$–$C_6$alkyl, $C_1$–$C_6$alkoxy, $C_1$–$C_6$alkylamino, —CN or —$NO_2$, $R_5$ and $R_6$ are each independently of the other hydrogen, $C_1$–$C_{18}$alkyl, $C_5$–$C_6$cycloalkyl; phenyl or naphthyl which is unsubstituted or substituted by halogen, $C_1$–$C_6$alkyl, $C_1$–$C_6$alkoxy, $C_4$–$C_6$alkylamino, —CN or —$NO_2$, or a group —$(CH_2)_n$—$SO_3R_7$, wherein $R_7$ is hydrogen, potassium or sodium, and n is an integer from 2 to 6, or $R_5$ and $R_6$, together with the linking nitrogen atom, are an unsubstituted or $C_1$–$C_6$alkyl- or phenyl-substituted 5- or 6-membered heterocyclic radical selected from the group consisting of pyrrolidinyl, piperidyl, pyrrolyl, triazolyl, imidazolyl, pyrazolyl, piperazinyl, morpholinyl, thiomorpholinyl, phthalimidyl, carbazolyl, indolyl, indazolyl, benzimidazolyl and tetrahydroquinolinyl, Y is $R_3$ or

and

Z is halogen.

Should some substituents be defined as halogen, they are typically iodo, fluoro, chloro or bromo, preferably bromo or chloro;

$C_1$–$C_4$alkyl is methyl, ethyl, n-propyl, isopropyl, n-butyl, sec-butyl, i-butyl or tert-butyl;

$C_1$–$C_6$alkyl is typically methyl, ethyl, n-propyl, isopropyl, n-butyl, sec-butyl, tert-butyl, n-amyl, tert-amyl, hexyl, and $C_1$–$C_{18}$alkyl is additionally e.g. heptyl, octyl, 2-ethylhexyl, nonyl, decyl, dodecyl, tetradecyl, hexadecyl or octadecyl;

$C_1$–$C_6$alkoxy is typically methoxy, ethoxy, n-propoxy, isopropoxy, butyloxy, or hexyloxy;

$C_1$–$C_{18}$alkylmercapto is typically methylmercapto, ethylmercapto, propylmercapto, butylmercapto or hexylmercapto;

$C_1$–$C_6$alkylamino is typically methylamino, ethylamino, propylamino or hexylamino;

$C_5$–$C_6$cycloalkyl is typically cyclopentyl and, preferably, cyclohexyl.

The process of this invention is particularly interesting using compounds of formulae I, II and III, wherein $R_1$, $R_2$ and $R_3$ are each independently of one another hydrogen, chloro, bromo, methyl, ethyl, methoxy, ethoxy, methylamino, ethylamino, —CN, —$NO_2$, phenyl or phenoxy, X is X', X' is —$OR_4$ or —$N(R_5)(R_6)$, wherein $R_4$ is methyl, ethyl, cyclohexyl; phenyl which is unsubstituted or substituted by chloro, methyl, methoxy, ethoxy, —CN, —$NO_2$ or dimethylamino, $R_5$ and $R_6$ are each independently of the other hydrogen, methyl, ethyl, cyclohexyl; phenyl which is unsubstituted or substituted by chloro, methyl, ethyl, methoxy, ethoxy, dimethylamino or —NO$_2$, or R$_5$ and R$_6$, together with the linking nitrogen atom, are a heterocyclic ring selected from the group consisting of pyrrolidinyl, morpholinyl or phthalimidyl, Y is

and

Z is chloro or bromo.

In formulae I and II, A is preferably a direct bond, R$_1$ and R$_2$ are preferably identical, and R$_3$ is preferably chloro, bromo or C$_1$–C$_4$alkyl.

Alkali metal formate or alkaline earth metal formate can be sodium formate, potassium formate, magnesium formate and calcium formate, preferably calcium formate, in the amounts stated for compounds X'—H of formula Ill. The formates can also act as bases.

Compounds of formula II are known or can be prepared by known methods such as described in U.S. Pat. Nos. 4,415,685, 4,579,949 and 4,791,204 mentioned at the outset, in particular in U.S. Pat. No. 4,579,949.

It has been found that the molar ratio of diketopyrrolopyrroles of formula II to formic acid or X'—H may vary in a wide range. To prevent impurities, a lower limit of 1:1 is recommended, or of 1:2, if Y in formula II is —COX. In the case of reactions with X'—H compounds of low molar weight, such as methanol, the molar ratio of diketopyrrolopyrroles of formula II to X'—H can become very small, in particular if it is desired that compound X'—H should also act as solvent.

In a preferred embodiment of this invention, the molar ratio of diketopyrrolopyrroles of formula II to formic acid or X'—H or to alkali metal formate or alkaline earth metal formate is chosen in the range from 1:1 to 1:1000, preferably from 1:1 to 1:20, or, if Y in formula II is

in the range from 1:2 to 1:2000, preferably from 1:4 to 1:40.

It has also been found that the carboxylation can preferably be carried out in an organic solvent.

Suitable solvents are usually all customary, preferably polar, organic solvents, aprotic or protic, more preferred aprotic polar solvents, or mixtures of such solvents with one another or with water, preferably those wherein at least one solvent is polar. It is convenient to use, for example, N-methylpyrrolidone, dimethylformamide or dimethylacetamide, preferably N-methylpyrrolidone.

It is usually possible to carry out the reaction in the presence of those known catalysts which assist a reaction of the inventive kind.

In a preferred embodiment of this invention, the catalysts are palladium catalysts. Suitable catalysts are usually the commonly known mono- or polydentate complexes of palladium, preferably with tertiary phosphines, such as those of formulae

 (IV)

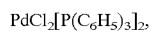 (V)

 (VI)

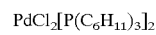 (VII)

and

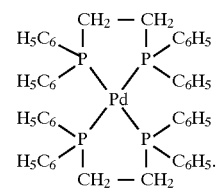 (VIII)

The palladium catalyst can be, and is preferably, prepared also in situ from a suitable palladium salt, such as palladium chloride and palladium acetate, and a tertiary phosphine, such as triphenylphosphine, tricyclohexylphosphine and bis(diphenylphosphino)ethane.

The use of palladium(II) chloride and triphenylphosphine is particularly preferred.

The catalyst is preferably used in an amount of 0.01 to 50 mol %, preferably of 0.1 to 30 mol %, based on the diketopyrrolopyrrole of formula II.

It has furthermore been found that, under certain circumstances, the inventive reaction may advantageously be carried out in the presence of a base. The invention therefore also relates to the novel reaction described above which is carried out in the presence of a base.

Suitable bases are, for example, tertiary amines, such as triethylamine, tripropylamine, tributylamine, N-methylpiperidine, N-methylmorpholine or benzyldimethylamine, and also alkali metal salts or alkaline earth metal salts of carboxylic acids containing 1–4 carbon atoms, such as sodium acetate, potassium acetate, sodium formate, potassium formate and calcium formate, as well as alkali metal salts or alkaline earth metal salts of weak mineral acids, such as potassium phosphate or sodium phosphate.

If the carboxylation is carried out using a primary or secondary amine of formula X'—H (III), wherein X' is —N(R$_5$)(R$_6$), then an excess of this amine can also serve as a base. In this case it is preferred to use 1 to 20 mol, preferably 2 to 10 mol, of an excess, based on the diketopyrrolopyrrole II used, or 1 to 40 mol, preferably 4 to 20 mol, if the diketopyrrolopyrrole II used contains two —COX-groups.

It is preferred to use a tertiary amine, preferably triethylamine.

The base is conveniently added in an amount of 1 to 20, preferably of 1 to 4, molar equivalents, based on the diketopyrrolopyrrole of formula II, if Y is R$_3$, and in an amount of 2 to 40, preferably of 2 to 10, molar equivalents, if Y is

The novel process is preferably carried out at a pressure in the range from 100 kPa (1 bar) to 10 MPa, preferably from 100 kPa to 5 MPa (50 bar), and at a temperature from 10° to 220°, preferably from 50° to 200°, more preferred from 100° to 180° C. The reaction is particularly preferably carried out at a carbon monoxide partial pressure in the range from 0.1 to 5 MPa, preferably from 0.5 to 2.5 MPa, if the carboxylation is carried out using compound X'—H of formula III.

As may be found already in U.S. Pat. Nos. 4,415,685, 4,579,949, 4,791,204 and 5,476,886 mentioned at the outset, the diketopyrrolopyrrolecarboxylic acids, diketopyrrolopyrrolecarboxylates and diketopyrrolopyrrolecarboxamides have good pigment properties and are therefore very well suited for pigmenting high molecular weight organic material. They are distinguished in particular by having high chroma.

Depending on their application, the compounds prepared according to this invention can be used as pigments directly after synthesis or after a customary and commonly known post-treatment.

The following Examples illustrate the invention in more detail.

EXAMPLE 1

An autoclave is charged with 4.46 g of the compound of formula

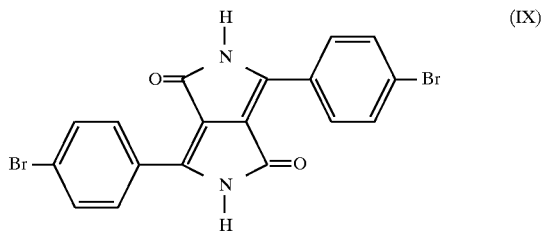

and 0.18 g of palladium(II) chloride, 1.58 g of triphenylphosphine, 6 ml of triethylamine, 10 ml of methanol and 180 ml of N-methylpyrrolidone. After expelling the air with nitrogen, 10 bar of carbon monoxide are forced in and the mixture is then heated, with stirring, for 24 hours to 120° C.

The suspension so obtained is poured on 1 l of water and the precipitate is then isolated by filtration and washed in succession with water, methanol and methyl-tert-butyl ether. Drying at 60° C. under vacuum gives 3.4 g (84%) of the pigment of formula

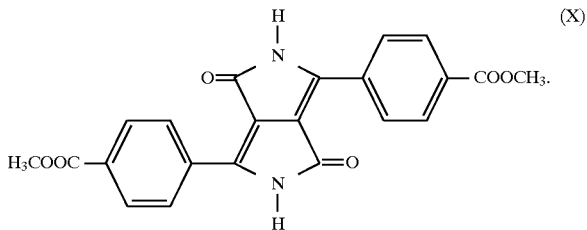

EXAMPLE 2

An autoclave is charged with 4.46 g of the compound of formula IX and 0.18 g of palladium(II) chloride, 1.58 g of triphenylphosphine, 10 ml of n-butylamine and 180 ml of N-methylpyrrolidone. After expelling the air with nitrogen, 10 bar of carbon monoxide are forced in and the mixture is then heated, with stirring, for 24 hours to 120° C.

The suspension so obtained is poured on 1 l of water and the precipitate is then isolated by filtration and washed in succession with water, methanol and methyl-tert-butyl ether. Drying at 60° C. under vacuum gives 4.24 g (87%) of the pigment of formula

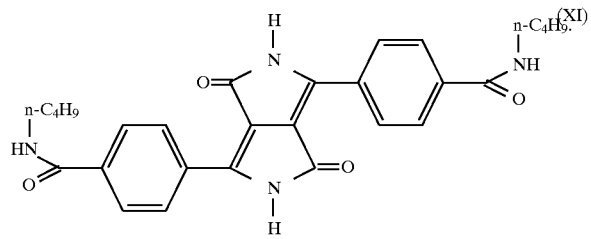

EXAMPLE 3

An autoclave is charged with 4.46 g of the compound of formula IX and 0.18 g of palladium(II) chloride, 1.58 g of triphenylphosphine, 6 ml of triethylamine, 4 m of aniline and 250 ml of N-methylpyrrolidone. After expelling the air with nitrogen, 10 bar of carbon monoxide are forced in and the mixture is heated, with stirring, for 40 hours to 120° C.

The suspension so obtained is poured on 1 l of water and the precipitate is then isolated by filtration and washed in succession with water, methanol and methyl-tert-butyl ether. Drying at 60° C. under vacuum gives 4.65 g (88%) of the pigment of formula

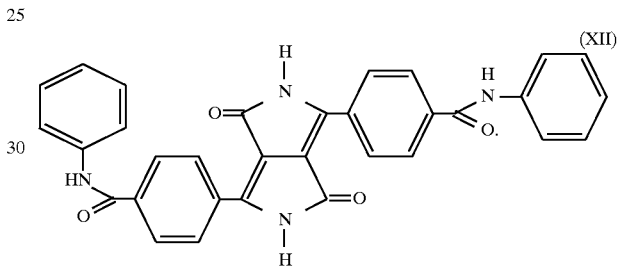

EXAMPLE 4

An autoclave is charged with 4.46 g of the compound of formula IX and 0.18 g of palladium(II) chloride, 1.58 g of triphenylphosphine, 5.0 g of 2-aminoethanesulfonic acid, 15 ml of triethylamine and 180 ml of N-methylpyrrolidone. After expelling the air with nitrogen, 10 bar of carbon monoxide are forced in and the mixture is then heated, with stirring, for 24 hours to 120° C.

The suspension so obtained is poured on a solution consisting of 8 ml of conc. sulfuric acid in 500 ml of water and the resulting solution is heated to 60° C. and charged with 160 g of NaCl. The precipitate is isolated by filtration and first washed with a saturated aqueous NaCl solution until free from acid and then it is washed with water free from salt, until the filtrate starts to turn red. Drying at 80° C. under vacuum gives 4.93 g (78%) of the pigment of formula

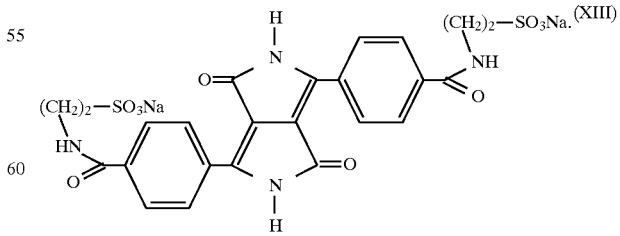

EXAMPLE 5

An autoclave is charged with 4.46 g of the p-dibromo compound (IX) (see Example 1) and 0.18 g of palladium(II)

chloride, 1.58 g of triphenylphosphine, 1.56 g of calcium formate and 200 ml of N-methylpyrrolidone. After expelling the air with nitrogen, 5 bar of carbon monoxide are forced in and the mixture is then heated, with stirring, for 24 hours to 120° C.

The suspension so obtained is filtered and the residue is washed with 200 ml of water, then with 200 ml of 5% aqueous sulfuric acid and then again with water until the filtrate is neutral, and the product is then dried under vacuum at 60° C. The filtrate is poured on 250 ml of water and the resultant precipitate is washed with 200 ml of 5% aqueous sulfuric acid and then with water until the filtrate is neutral, and the product is then dried at 60° C. under vacuum.

The combined products so obtained are then extracted with 50 ml of methyl-tert-butyl ether and the residue is dried at 70° C. under vacuum.

3.5 g (93%) of the pigment of formula

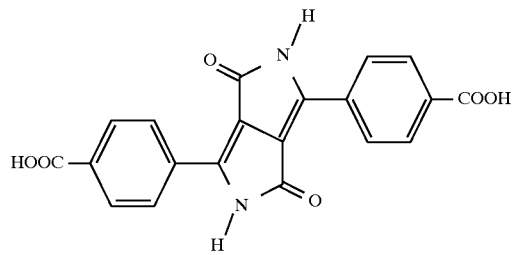

are obtained.

EXAMPLE 6

An autoclave is charged with 8.92 g of the p-dibromo compound of formula (IX) and 0.36 g of palladium(II) chloride, 3.16 g of triphenylphosphine, 5.44 g of imidazole, 12 ml of triethylamine and 320 ml of N-methylpyrrolidone. After expelling the air with nitrogen, 10 bar of carbon monoxide are forced in and the mixture is then heated, with stirring, for 24 hours to 120° C.

The suspension so obtained is poured on 1 l of toluene and the precipitate is isolated by filtration and stirred for 1 hour with 130 ml of methylene chloride. This mixture is then filtered again and the product is washed with 50 ml of ether and dried at 60° C. under vacuum.

7.0 g (74%) of the pigment of formula

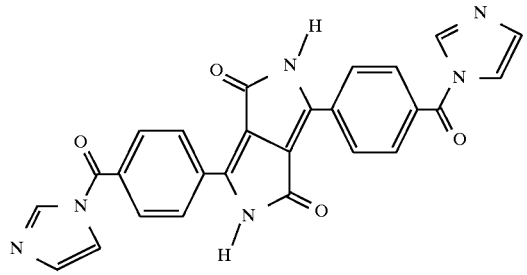

are obtained.

What is claimed is:
1. A process for the preparation of a diketopyrrolopyrrole of formula

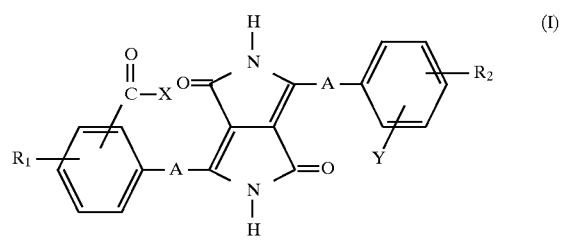

by reacting a diketopyrrolopyrrole of formula II

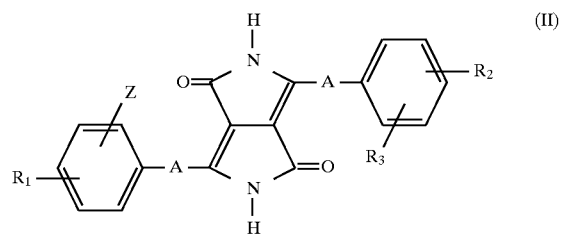

with
a) formic acid or
b) a compound of formula III

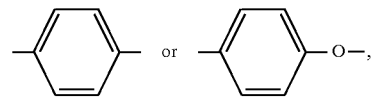

or an alkali metal formate or alkaline earth metal formate together with carbon monoxide
in the presence of a catalyst,
wherein, in formulae I, II and III,
A is a direct bond or a group wherein phenylene is bound to the pyrrolopyrrole,
$R_1$, $R_2$ and $R_3$ are each independently of one another hydrogen, halogen, $C_1$–$C_6$alkyl, $C_5$–$C_6$-cycloalkyl, $C_1$–$C_6$alkoxy, $C_1$–$C_6$alkylamino, $C_1$–$C_6$alkylmercapto, —$CF_3$, —CN or —$NO_2$,
X is X' or OH,
X' is —$OR_4$ or —$N(R_5)(R_6)$, wherein
$R_4$ is $C_1$–$C_{18}$alkyl, $C_5$–$C_6$cycloalkyl; phenyl or naphthyl which is unsubstituted or substituted by halogen, $C_1$–$C_6$alkyl, $C_1$–$C_6$alkoxy, $C_1$–$C_6$alkylamino, —CN or —$NO_2$,
$R_5$ and $R_6$ are each independently of the other hydrogen, $C_1$–$C_{18}$alkyl, $C_5$–$C_6$cycloalkyl; phenyl or naphthyl which is unsubstituted or substituted by halogen, $C_1$–$C_6$alkyl, $C_1$–$C_6$-alkoxy, $C_4$–$C_6$alkylamino, —CN or —$NO_2$, or a group —$(CH_2)_n$—$SO_3R_7$, wherein $R_7$ is hydrogen, potassium or sodium, and n is an integer from 2 to 6, or $R_5$ and $R_6$, together with the linking nitrogen atom, are an unsubstituted or $C_1$–$C_6$alkyl- or phenyl-substituted 5- or 6-membered heterocyclic radical selected from the group consisting of pyrrolidinyl, piperidyl, pyrrolyl, triazolyl, imidazolyl, pyrazolyl, piperazinyl, morpholinyl, thiomorpholinyl, phthalimidyl, carbazolyl, indolyl, indazolyl, benzimidazolyl and tetrahydroquinolinyl, Y is $R_3$ or

and

Z is halogen.

2. A process for the preparation of a diketopyrrolopyrrole of formula I according to claim 1, wherein the catalyst is a palladium catalyst.

3. A process for the preparation of a diketopyrrolopyrrole of formula I according to claim 1, which comprises carrying out the reaction in the presence of a base.

4. A process for the preparation of a diketopyrrolopyrrole of formula I according to claim 2, which comprises carrying out the reaction in the presence of a base.

5. A process for the preparation of a diketopyrrolopyrrole of formula I according to claim 1, which comprises carrying out the reaction in an organic solvent.

6. A process for the preparation of a diketopyrrolopyrrole of formula I according to claim 2, which comprises carrying out the reaction in an organic solvent.

7. A process for the preparation of a diketopyrrolopyrrole of formula I according to claim 3, which comprises carrying out the reaction in an organic solvent.

8. A process for the preparation of a diketopyrrolopyrrole of formula I according to claim 4, which comprises carrying out the reaction in an organic solvent.

9. A process for the preparation of a diketopyrrolopyrrole of formula I according to claim 1, which comprises choosing the molar ratio of diketopyrrolopyrroles of formula II to formic acid or X'—H or to alkali metal formate or alkaline earth metal formate in the range from 1:1 to 1:1000 or, if Y in formula II is

in the range from 1:2 to 1:2000.

10. A process for the preparation of a diketopyrrolopyrrole of formula I according to claim 8, which comprises choosing the molar ratio of diketopyrrolopyrroles of formula II to formic acid or X'—H or to alkali metal formate or alkaline earth metal formate in the range from 1:1 to 1:1000 or, if Y in formula II is

in the range from 1:2 to 1:2000.

11. A process according to claim 1, wherein, if X' is an amino group —N($R_5$)($R_6$), an excess of the compound of formula III is used as base.

12. A process according to claim 1, which comprises carrying out the reaction at a carbon monoxide partial pressure in the range of 0.1 to 5 MPa.

13. A process according to claim 10, which comprises carrying out the reaction at a carbon monoxide partial pressure in the range of 0.1 to 5 MPa.

\* \* \* \* \*